US010413224B2

(12) United States Patent
Yang

(10) Patent No.: US 10,413,224 B2
(45) Date of Patent: Sep. 17, 2019

(54) ANALYTE SENSING SYSTEM

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 499 days.

(21) Appl. No.: 14/907,151

(22) PCT Filed: Apr. 18, 2014

(86) PCT No.: PCT/CN2014/075654
§ 371 (c)(1),
(2) Date: Jan. 22, 2016

(87) PCT Pub. No.: WO2015/131432
PCT Pub. Date: Sep. 11, 2015

(65) Prior Publication Data
US 2016/0157759 A1   Jun. 9, 2016

(30) Foreign Application Priority Data
Mar. 7, 2014   (CN) .......................... 2014 1 0083260

(51) Int. Cl.
*A61B 5/145*   (2006.01)
*A61B 5/1473*   (2006.01)
*A61B 5/00*   (2006.01)

(52) U.S. Cl.
CPC ........ *A61B 5/14503* (2013.01); *A61B 5/0002* (2013.01); *A61B 5/0022* (2013.01);
(Continued)

(58) Field of Classification Search
CPC . A61B 5/14503; A61B 5/0002; A61B 5/0022; A61B 5/14532; A61B 5/6801;
(Continued)

(56) References Cited

U.S. PATENT DOCUMENTS 5,924,996 A   7/1999   Cho
5,975,305 A   11/1999   Barger
(Continued)

FOREIGN PATENT DOCUMENTS

CN   1636505 A   7/2005
CN   101125086 A   2/2008
(Continued)

OTHER PUBLICATIONS

Internal Search Report for PCT/CN2014/075654, dated Nov. 21 2014, ISA/CN.
(Continued)

*Primary Examiner* — Navin Natnithithadha
(74) *Attorney, Agent, or Firm* — Yue (Robert) Xu; Apex Attorneys at Law, LLP

(57) ABSTRACT

Disclosed is an analyte sensing system (1), comprising: a sensor probe (11) for collecting the analyte content in human body and transmitting the collected analyte content information; a transmitter (13) connected to the sensor probe (11) for receiving the analyte content information transmitted by the sensor probe (11) implanted subcutaneously and converting same into a radio signal to output; and a receiver for receiving the radio signal comprising the analyte content information transmitted by the transmitter (13) and converting same into analyte content data to display to the user. The analyte sensing system (1) uses an automatic installer (122) to implant the sensor probe (11) into the human body, and obtains the analyte content information collected by the sensor probe (11) through the transmitter (13) and the receiver. The analyte sensing system (1) has a small structure, and is easy to use and convenient to operate.

19 Claims, 17 Drawing Sheets

(52) U.S. Cl.
CPC ........ *A61B 5/1473* (2013.01); *A61B 5/14532* (2013.01); *A61B 5/6801* (2013.01); *A61B 5/742* (2013.01); *A61B 2560/045* (2013.01)

(58) Field of Classification Search
CPC . A61B 5/742; A61B 2560/045; A61B 5/1473; A61B 5/1468
USPC .......................................... 600/309, 345–366
See application file for complete search history.

(56) References Cited

U.S. PATENT DOCUMENTS

| | | | |
|---|---|---|---|
| 7,381,184 B2* | 6/2008 | Funderburk | A61B 5/14532 600/300 |
| 7,494,465 B2* | 2/2009 | Brister | A61B 5/14532 600/300 |
| 7,768,386 B2* | 8/2010 | Hayter | G06F 19/00 340/501 |
| 7,905,833 B2* | 3/2011 | Brister | A61B 5/14532 600/309 |
| 9,101,306 B2* | 8/2015 | Bernini | A61B 5/0031 |
| 9,451,910 B2* | 9/2016 | Brister | A61B 5/1411 |
| 9,668,682 B2* | 6/2017 | Brister | A61B 5/1411 |
| 9,775,543 B2* | 10/2017 | Brister | A61B 5/1451 |
| 9,801,572 B2* | 10/2017 | Brister | A61B 5/14532 |
| 9,814,414 B2* | 11/2017 | Brister | A61B 5/14532 |
| 9,833,176 B2* | 12/2017 | Brister | A61B 5/6849 |
| 2006/0016700 A1* | 1/2006 | Brister | A61B 5/14532 205/777.5 |
| 2006/0020186 A1 | 1/2006 | Brister et al. | |
| 2006/0195029 A1* | 8/2006 | Shults | A61B 5/0002 600/345 |
| 2006/0200020 A1* | 9/2006 | Brister | A61B 5/0031 600/345 |
| 2006/0224141 A1 | 10/2006 | Rush et al. | |
| 2006/0229512 A1* | 10/2006 | Petisce | A61B 5/14532 600/347 |
| 2007/0173710 A1* | 7/2007 | Petisce | A61B 5/14532 600/345 |
| 2007/0208245 A1* | 9/2007 | Brauker | A61B 5/14532 600/365 |
| 2007/0208246 A1* | 9/2007 | Brauker | A61B 5/0031 600/365 |
| 2008/0242961 A1* | 10/2008 | Brister | A61B 5/0002 600/345 |
| 2009/0076360 A1* | 3/2009 | Brister | A61B 5/1411 600/365 |
| 2010/0094110 A1 | 4/2010 | Heller et al. | |
| 2010/0198142 A1 | 8/2010 | Sloan et al. | |
| 2010/0324403 A1* | 12/2010 | Brister | A61B 5/1411 600/365 |
| 2011/0190603 A1* | 8/2011 | Stafford | A61B 5/14532 600/309 |
| 2012/0245447 A1 | 9/2012 | Karan et al. | |
| 2013/0331676 A1* | 12/2013 | Morgan | G01R 35/00 600/365 |

FOREIGN PATENT DOCUMENTS

| | | |
|---|---|---|
| CN | 101166466 A | 4/2008 |
| CN | 101180093 A* | 5/2008 |
| CN | 101686811 A | 3/2010 |
| CN | 201453279 U | 5/2010 |
| CN | 201453297 U | 5/2010 |
| CN | 101843505 A | 9/2010 |
| CN | 102008290 A | 4/2011 |
| CN | 201949010 U | 8/2011 |
| CN | 102472719 A | 5/2012 |
| CN | 102883656 A | 1/2013 |
| CN | 103300866 A | 9/2013 |
| CN | 103330567 A | 10/2013 |
| CN | 103619255 A | 3/2014 |
| WO | 2008115409 A1 | 9/2008 |
| WO | 2009105709 A1 | 8/2009 |
| WO | 2011041449 A1 | 4/2011 |

OTHER PUBLICATIONS

European Search Report for 14884519.1-1657/3040025, dated Mar. 10, 2017.

English Translation of the 1st Office Action for 201410083260.X, dated Apr. 5, 2017.

* cited by examiner

ANALYTE SENSING SYSTEM

CROSS-REFERENCE TO RELATED APPLICATIONS

The present application is a national phase of International Application No. PCT/CN2014/075654, filed on Apr. 18, 2014, which claims priority to Chinese Patent Application No. 201410083260.X, filed on Mar. 7, 2014, and entitled "ANALYTE SENSING SYSTEM", the entire disclosure of which is incorporated herein by reference.

TECHNICAL FIELD

The present disclosure generally relates to the field of medical appliance, and more particularly, to an analyte sensing system.

BACKGROUND

A pancreas in a normal human body may automatically monitor the changes of glucose in the blood, and may automatically secrete insulin required. However, a pancreas in a diabetic patient cannot secrete the insulin required as normal, in other words, the pancreatic function is abnormal. Diabetes is a metabolic disease caused by pancreatic dysfunction. Diabetes is a lifelong disease which can't be cured by current medical technology. The only way to control diabetes and the initiation and developments of its complications is stabilizing glucose.

Conventionally, glucose detection usually uses a test strip and a glucose monitor, and blood glucose is detected by a magnitude of current produced as a result of reactions between glucose in blood and glucose oxidase in the test strip. The conventional glucose detection usually uses blood quickly sampled from a finger tip to detect the glucose. Repeated acupunctures are required to collect blood, besides, instantaneous glucose is normally detected at seven time of a day, including empty stomach, after breakfast, before lunch, after lunch, before dinner, after dinner, and before sleep. The instantaneous glucose is likely to be influenced by many factors such as movement, diet, drug, mood swing, etc. The instantaneous glucose only reflects glucose situation at several time points of a day, which means it has one-sidedness and inaccuracy. For understanding the status of glucose, the instantaneous glucose is on the basis of one-sided viewpoint, and cannot reflect all-day glucose situation of the diabetic patient, so asymptomatic hypoglycemia and hyperglycemia are difficult to be found. For a patient with large glucose fluctuations, the instantaneous glucose values are not enough to provide accurate medication basis for a doctor. Moreover, the test strip for detecting may be influenced by temperature, humidity and chemical substances in the detection environment. If the test strip is undeservedly stored, it will cause a large detection error. Further, if the blood is insufficient in the process of detecting, it will lead to a detection failure or a low detection result, and a new test strip is needed for redetermination. If the blood drop is too large and overflows the detection area, it will also affect the detection result.

A sensor probe is a kind of detecting device which can sense information of substances to be detected, convert the information into an electrical signal or other information with a desired form according to a certain rule, and output the converted information. A sensor probe is used for information transmission, information processing, information storage, information display, information recording and information controlling, and thus is very important for realizing automatic detection and automatic control. A continuous glucose monitoring system indicates a device that can continuously monitor the changes of glucose by using a glucose sensor probe implanted in the subcutaneous tissue of a patient. The continuous glucose monitoring system mainly includes a glucose sensor probe and an electronic device configured to record and display. The continuous glucose monitoring system has the advantages of small size, portability, etc. Considering the comfort level of patients when they are wearing the glucose sensor probe, the glucose sensor probe is made of slender and soft medical polymer materials. When glucose is to be detected, the glucose sensor probe is implanted subcutaneously into the patient. The continuous glucose monitoring system continuously monitors the changes of glucose and draw a curve representing the changes of glucose, which can provide an important reference for rational therapy. Furthermore, the continuous glucose monitoring system can make an alarm to the user when an abnormal event such as hypoglycemia, hyperglycemia, etc. occurs, which will help to take response measures quickly and avoid treatment delay.

The continuous glucose monitoring system has following advantages.

The continuous glucose monitoring system can obtain a chart representing the changes of glucose, and other control information which are more comprehensive and accurate.

The continuous glucose monitoring system can identify glucose fluctuations caused by following conditions: food type, movement type and intensity, drug (includes insulin) effect, labour intensity, mode of life, etc.

The continuous glucose monitoring system can help people to understand factors that influence diabetes control, reasons that cause hypoglycemia, situations when asymptomatic hypoglycemia may happen, response measures that patient would take for different conditions, hyperglycemia, and so on.

The continuous glucose monitoring system can strengthen the treatment of the diabetic patient, help doctors to adjust therapeutic schedules, and provide help in analyzing individual or regular glucose fluctuations.

SUMMARY

Regarding the above-mentioned shortcomings of the prior art, an object of the present disclosure is to provide an analyte sensing system which may be more conveniently used.

In order to achieve the above-mentioned purposes and other related purposes, the present disclosure provides an analyte sensing system, including: a sensor probe, configured to detect content of an analyte in a human body and transmit detected content information of the analyte; a transmitter connected to the sensor probe, configured to receive the analyte content information transmitted by the sensor probe implanted subcutaneously, convert the analyte content information into a radio signal and output the radio signal; and a receiver, configured to receive the radio signal including the analyte content information transmitted by the transmitter, convert the analyte content information into analyte content data and display the analyte content data to a user.

Optionally, the analyte sensing system further includes a probe installation device configured to implant the sensor probe into a subcutis of the human body, wherein the probe installation device includes a support mount, an inserter, a safety lock and a medical adhesive tape, wherein the support mount includes a first installation structure configured to accommodate the inserter, a second installation structure configured to accommodate the transmitter, and a third installation structure configured to accommodate a sensor probe shell; wherein the inserter is located on the first installation structure, and the inserter includes an inserter shell, an ejection mechanism arranged inside the inserter shell, and a button module configured to release the ejection mechanism; wherein the safety lock is located on the inserter shell and configured to cover the button module; and wherein the medical adhesive tape is connected to the support mount and configured to stick the support mount to a skin of the human body.

Optionally, the first installation structure includes a first sliding unit, a second sliding unit and a first fastener unit; the inserter shell includes a third sliding unit, a fourth sliding unit and a second fastener unit arranged on the bottom edge of the inserter shell, wherein the third sliding unit and the fourth sliding unit are corresponding to the first sliding unit and the second sliding unit, respectively, and the second fastener unit is corresponding to the first fastener unit.

Optionally, a flange and an operating unit are arranged on each of opposite inner sides of the second installation structure, a cantilever and a clamping hook are respectively arranged in front and rear ends of each of the operating units, when the rear ends of the operating units are pressed, the two cantilevers are driven to an open state; grooves corresponding to the flanges are respectively arranged on two sides of an outer edge of the transmitter, slots corresponding to the cantilevers and the clamping hooks are respectively arranged in front and rear ends of the transmitter.

Optionally, the third installation structure includes multiple fixture blocks, and the sensor probe shell is arranged in a structure formed by the multiple fixture blocks.

Optionally, a silica gel plug is arranged between the support mount and the sensor probe shell, and the silica gel plug is squeezed by the support mount and the sensor probe shell to form a sealed and waterproof structure.

Optionally, the transmitter has a seal cavity configured to accommodate the sensor probe shell.

Optionally, an electric conductor is arranged on the sensor probe shell, where the electric conductor is configured to, after the sensor probe and the transmitter are coupled, contact a connecting device in the transmitter to product a short signal for identifying a connection state of the sensor probe and the transmitter.

Optionally, an identification module configured to identify a connection state of the sensor probe and the transmitter is arranged on the support mount, wherein the identification module is a magnetic switch.

Optionally, a slot is arranged on the support mount, and a clamping hook corresponding to the slot is arranged on the safety lock.

Optionally, an operating handle configured to control the clamping hook to separate from the slot is arranged on the safety lock.

Optionally, the ejection mechanism includes: a first sliding block, including a hollow guide column which is vertically arranged, a needle bed parallel to the hollow guide column, and a first locking part located on an inner wall of the hollow guide column, wherein an ejection space is set in an interior of the hollow guide column; a second sliding block corresponding to the first sliding block, including a second locking part locked with the first locking part, wherein the second locking part penetrates through the interior of the hollow guide column; an inner spring located in the ejection space, wherein two ends of the inner spring resist against the first sliding block and the second sliding block, respectively, when the inner spring releases, the inner spring drives the first sliding block to rise; an outer spring arranged circumferentially outside of the hollow guide column, wherein two ends of the outer spring resist against the second sliding block and baffles located in the inserter shell, respectively, when the outer spring releases, the outer spring drives the ejection mechanism to descend; and a puncture needle, wherein a top of the puncture needle is fixed inside the needle bed, wherein a body of the puncture needle has a puncture part, the body of the puncture needle penetrates through the second sliding block and thus the puncture part of the puncture needle extends outside of the second sliding block, when the outer spring releases, the puncture needle extends out downwardly, and when the inner spring releases, the puncture needle is pulled back upwardlu.

Optionally, the sensor probe includes a sensing part configured to detect the analyte content in the human body and a connecting part connected to the transmitter, wherein the sensing part is arranged in the puncture part and is implanted subcutaneously with the aid of the puncture needle.

Optionally, the puncture part is located at an end of the puncture needle, and the cross section of the puncture part is curved.

Optionally, the button module includes two buttons located on the opposite sides of the inserter shell, when the buttons are triggered, the outer spring and the inner spring are respectively triggered to release.

Optionally, the first locking part and the second locking part are released to be unlocked when either of the buttons is pressed. That is, when the button is pressed, the outer spring is triggered to release, and then the first locking part and the second locking part are released to be unlocked, and then the inner spring is triggered to release.

Optionally, the probe installation device further includes an identity recognition module configured to recognize identity and store personalized information of the probe installation device, the sensor probe, or a combination thereof, wherein the identity recognition module is a near field communication (NFC) tag, a radio frequency identification (RFID) tag or an identity recognition chip.

Optionally, the identity recognition module is located between the medical adhesive tape and the support mount, or is embedded in the support mount.

Optionally, a processor and a control circuit are embedded in the transmitter.

Optionally, the receiver includes a display screen, a control circuit and a processor.

Optionally, the transmitter is configured to receive the analyte content information transmitted by the sensor probe, convert the analyte content information into a radio-frequency signal and output the radio-frequency signal.

The analyte sensing system further includes an automatic relay system configured to convert the radio-frequency signal into a 2G/3G signal, a Bluetooth signal, or a wireless fidelity (WIFI) signal.

Optionally, the automatic relay system further includes an alarm apparatus.

Optionally, the automatic relay system further includes a display screen.

As mentioned above, the analyte sensing system according to the present disclosure uses an inserter to implant the sensor probe into the human body, and obtains the analyte content information detected by the sensor probe through the transmitter and the receiver. The analyte sensing system

BRIEF DESCRIPTION OF REFERENCE SIGNS

Figure 1:
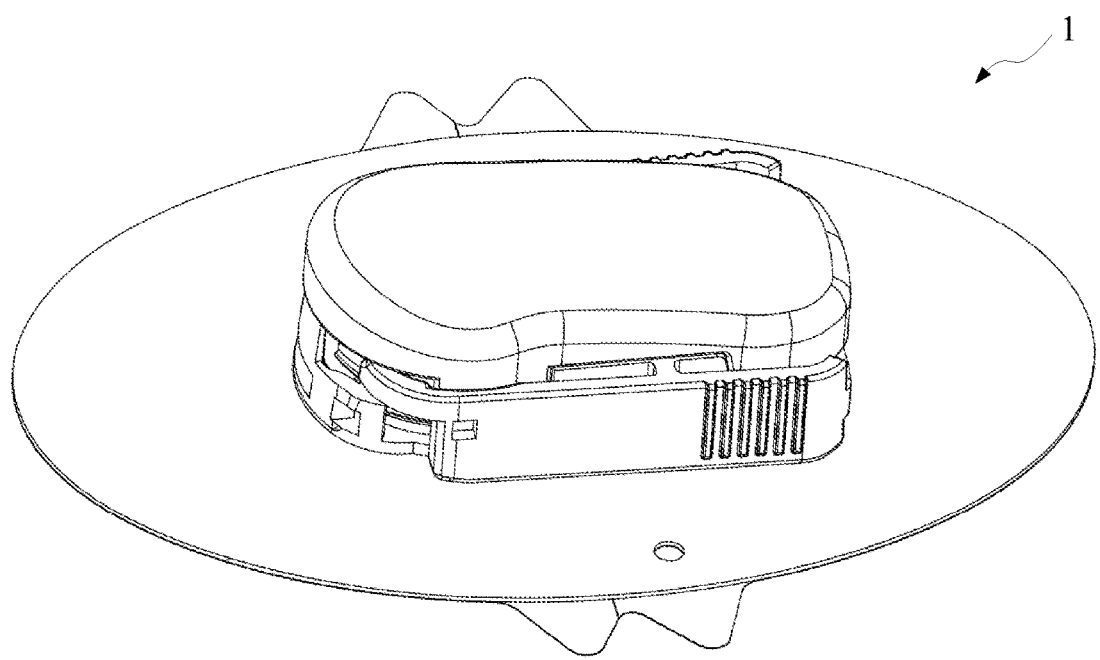
FIG. 1 illustrates a schematic diagram of an analyte sensing system according to present disclosure.

1 analyte sensing system
11 sensor probe
111 sensing part
112 connecting part
12 probe installation device
121 support mount
1211a first sliding unit
1211b second sliding unit
1212 first fastener unit
1213 flange
1214 clamping hook
1215 cantilever
1216 fixture block
1217 pressing unit
1218 slot
122 inserter
1221 installer shell
12211a third sliding unit
12211b fourth sliding unit
12212 second fastener unit
12213 baffle
1222 ejection mechanism
12221 first sliding block
122211 hollow guide column
122212 needle bed
122213 first locking part
12222 second sliding block
122221 second locking part
12223 inner spring
12224 outer spring
12225 puncture needle
122251 puncture part
1223 button module
12231 button support mount
123 safety lock
1231 clamping hook
1232 operating handle
124 medical adhesive tape
125 sensor probe shell
1251 clasp
1252 O-shaped sealing ring
126 silica gel plug
127 identity recognition module
128 identification module
13 transmitter
131 groove
132, 133 slot

DETAILED DESCRIPTION OF THE DISCLOSURE

The embodiments of the present disclosure are described in the following through specific examples, and those skilled in the art can easily understand other advantages and effects of the present disclosure according to the content disclosed in the specification.

Referring to the FIG. 1 to FIG. 21, it should be noted that, the structures, the scales, the sizes, like shown in the drawings, are only used to match the content disclosed in the specification, for being understood and read by those skilled in the art, instead of limiting limited implementation conditions of the present disclosure, and thus not have any essential technical meaning. Any modification in structure, change in scale, or adjustment in size should fall within the scope of the technical content disclosed by the present disclosure without influencing the generated efficacy and achieved objective of the present disclosure. Meanwhile, some words such as "upper", "lower", "left", "right", "middle", and "a" quoted in the specification are only used for clarity of the illustration instead of limiting the implementation scope of the present disclosure, and any change or adjustment of relative relationships should be considered as falling within the scope of implementation of the present disclosure without essentially changing the technical content.

The present disclosure provides an analyte sensing system, which is configured to real-timely and dynamically monitor change of an analyte content in human body by a glucose sensor probe implanted subcutaneously into the patient. That is, when glucose is detected, the glucose sensor probe is implanted subcutaneously into the patient, and the continuous glucose monitoring system will continuously monitor the changes of glucose and draw the change curve of glucose, and then provide an important clue for rational therapy. Referring to FIG. 1, a schematic diagram of an analyte sensing system according to present disclosure is illustrated, the analyte sensing system includes: a sensor probe 11, a transmitter 13 and a receiver. In some embodiments, the analyte in a human body is glucose in the human body; the analyte sensing system 1 is configured to real-timely and dynamically monitor change of glucose in human body by a glucose sensor probe 11 implanted subcutaneously into the patient. Therefore, we will take the analyte sensor probe that detects glucose content information in the human body as an example to illustrate in some embodiments described below.

Figure 2:
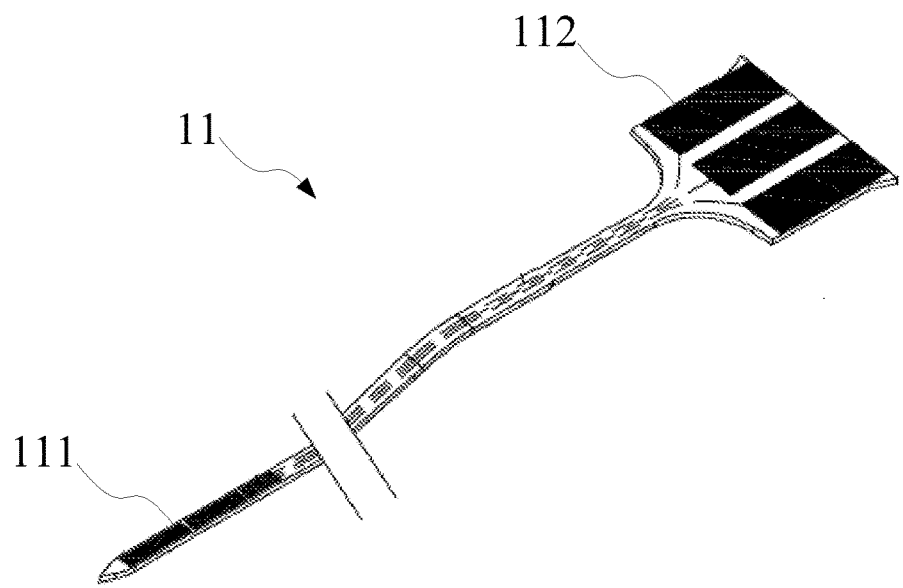
FIG. 2 illustrates a schematic diagram of a sensor probe in an analyte sensing system according to present disclosure.

The sensor probe 11 is configured to detect the analyte content in the human body and transmit the detected analyte content information. Referring to FIG. 2, a schematic diagram of a sensor probe in an analyte sensing system according to present disclosure is illustrated. As shown in FIG. 2, the sensor probe 11 includes a sensing part 111 configured to detect the analyte content in the human body and a connecting part 112 (PAD) connected to the transmitter, the sensing part 111 is arranged in the puncture needle and is implanted subcutaneously via the aid of the puncture needle.

The transmitter 13 and the sensor probe 11 achieve communication connection by the connecting part 112 (PAD) of the sensor probe 11. Where the transmitter 13 is configured to receive the glucose content information transmitted by the sensor probe 11 implanted subcutaneously, convert the glucose content information into a radio signal and output the radio signal, while the transmitter 13 is configured to receive the glucose content information transmitted by the sensor probe 11 implanted subcutaneously, convert the glucose content information into a radio-frequency signal (RF signal) and output the radio-frequency signal. A processor and a control circuit (not shown) are embedded in the transmitter 13.

In some embodiments, the analyte sensing system further includes an automatic relay system configured to convert the radio-frequency signal into a 2G/3G signal, a Bluetooth signal, or a wireless fidelity (WIFI) signal. In general, the transmitter transmits the signal directly to the receiver, and the receiver can receive and identify the signal. However, when the receiver cannot receive and identify the signal, the automatic relay system will be required to convert the signal into a signal that can be identified by the receiver. The automatic relay system and the transmitter realize communications via a radio signal.

In some embodiments, the automatic relay system further includes an alarm apparatus (not shown), and the automatic relay system may identify the abnormal event such as hypoglycemia, hyperglycemia, etc. and alarm the user. In addition, the automatic relay system further also includes a display screen (not shown) for displaying the abnormal event.

The receiver (not shown) is configured to receive the radio signal including the glucose content information transmitted by the transmitter, convert the radio signal into glucose content data and display the glucose content data to a user.

The receiver includes a display screen, a control circuit and a processor. The transmitter may transmit the glucose monitoring information detected by the sensor probe to the receiver by wireless transmission receive mode. The control circuit and the processor are built in the receiver, and the receiver displays the glucose monitoring information to the user in the form of glucose values through a certain algorithm. In some specific embodiments, the display screen may be a display screen support mountd on electronic paper breaking code display.

In some specific embodiments, the receiver may be a smart mobilephone with a glucose monitoring program APP (application), or other intelligent terminal that can receive the information of the receiver (e.g., PDA).

The present disclosure provides another analyte sensing system, which is configured to real-timely and dynamically monitor change of an analyte content in the human body by a glucose sensor probe implanted subcutaneously into the patient. That is, when glucose is detected, the glucose sensor probe is implanted subcutaneously into the patient, and the continuous glucose monitoring system will continuously monitor the changes of glucose and draw the change curve of glucose, and then provide an important clue for rational therapy. Referring to FIG. 1, a schematic diagram of an analyte sensing system according to present disclosure is illustrated, the analyte sensing system includes: a sensor probe 11, a probe installation device 12, a transmitter 13 and a receiver.

The sensor probe 11 is configured to detect the analyte content in the human body and transmit the detected analyte content information. Referring to FIG. 2, a schematic diagram of a sensor probe in an analyte sensing system according to present disclosure is illustrated. As shown in FIG. 2, the sensor probe 11 includes a sensing part 111 configured to detect the analyte content in the human body and a connecting part 112 (PAD) connected to the transmitter, the sensing part 111 is arranged in the puncture needle and is implanted subcutaneously via the aid of the puncture needle.

Figure 3:
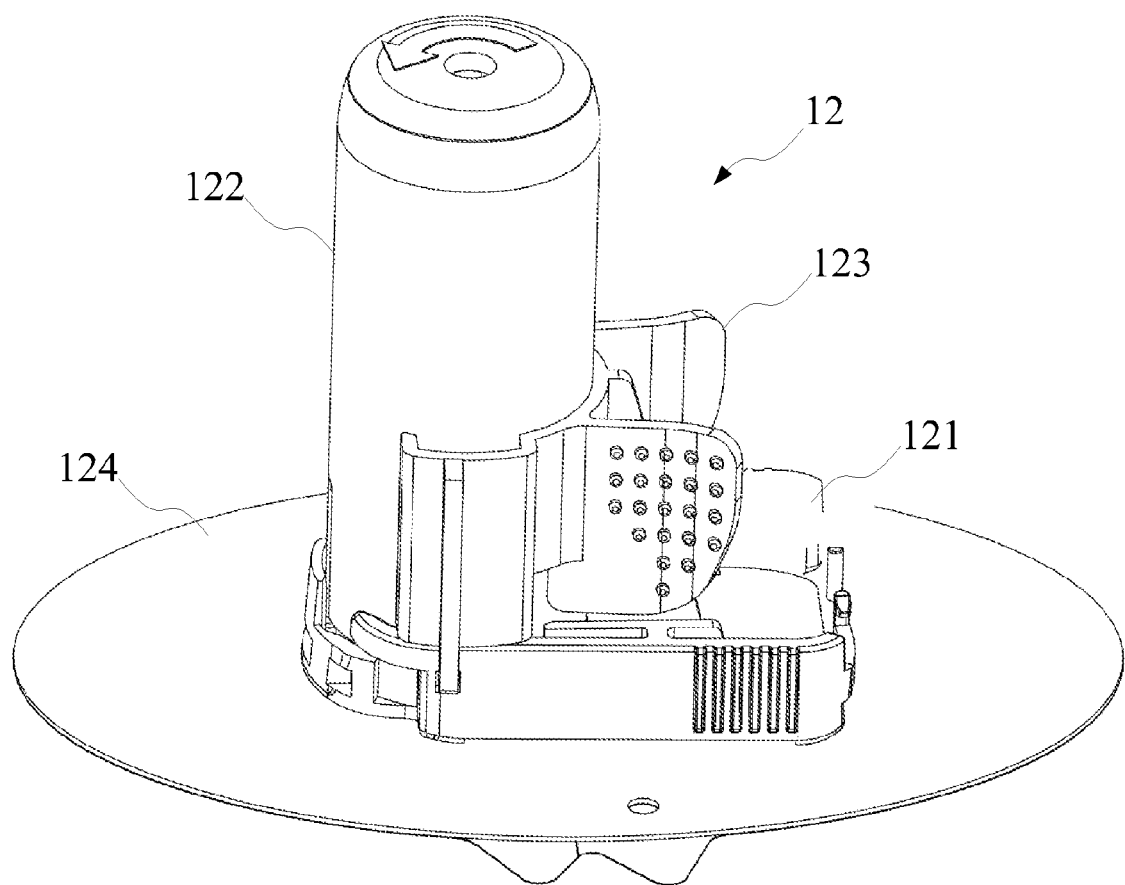
FIG. 3 illustrates a schematic diagram of a probe installation device in an analyte sensing system according to present disclosure.

The probe installation device 12 is configured to implant the sensor probe 11 into a subcutis of the human body. Referring to FIG. 3, a schematic diagram of a probe installation device in an analyte sensing system according to present disclosure is illustrated. As shown in FIG. 3, the probe installation device 12 includes: a support mount 121, an inserter 122, a safety lock 123 and a medical adhesive tape 124. The inserter 122 connects the transmitter to the sensor probe 11, after it completes the installation of the sensor probe 11.

Figure 4:
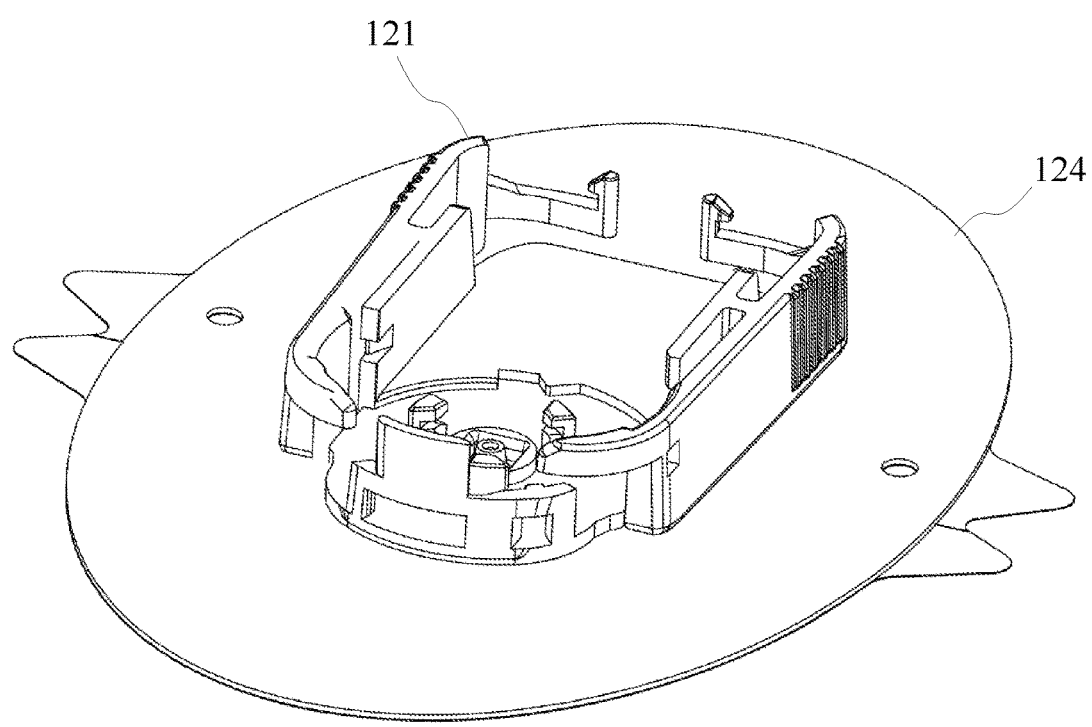
FIG. 4 illustrates a schematic diagram of a support mount in an analyte sensing system according to present disclosure.
Figure 5:
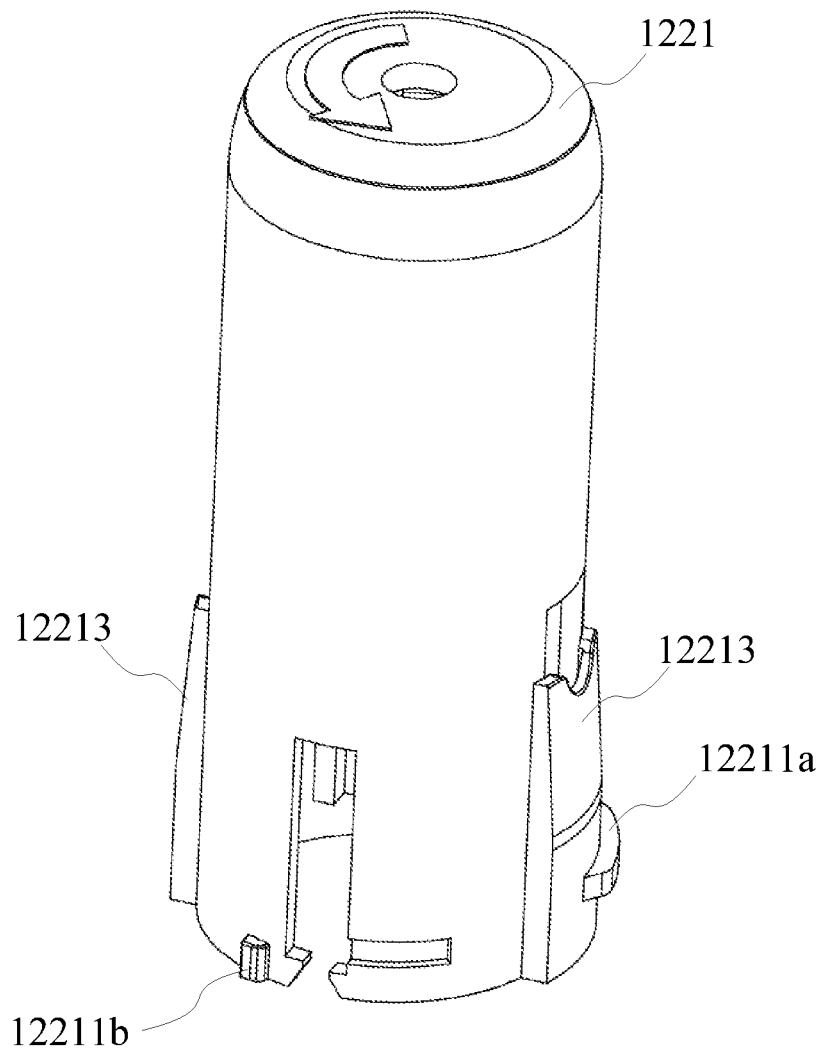
FIG. 5 illustrates a schematic diagram of a shell in an analyte sensing system according to present disclosure.
Figure 6:
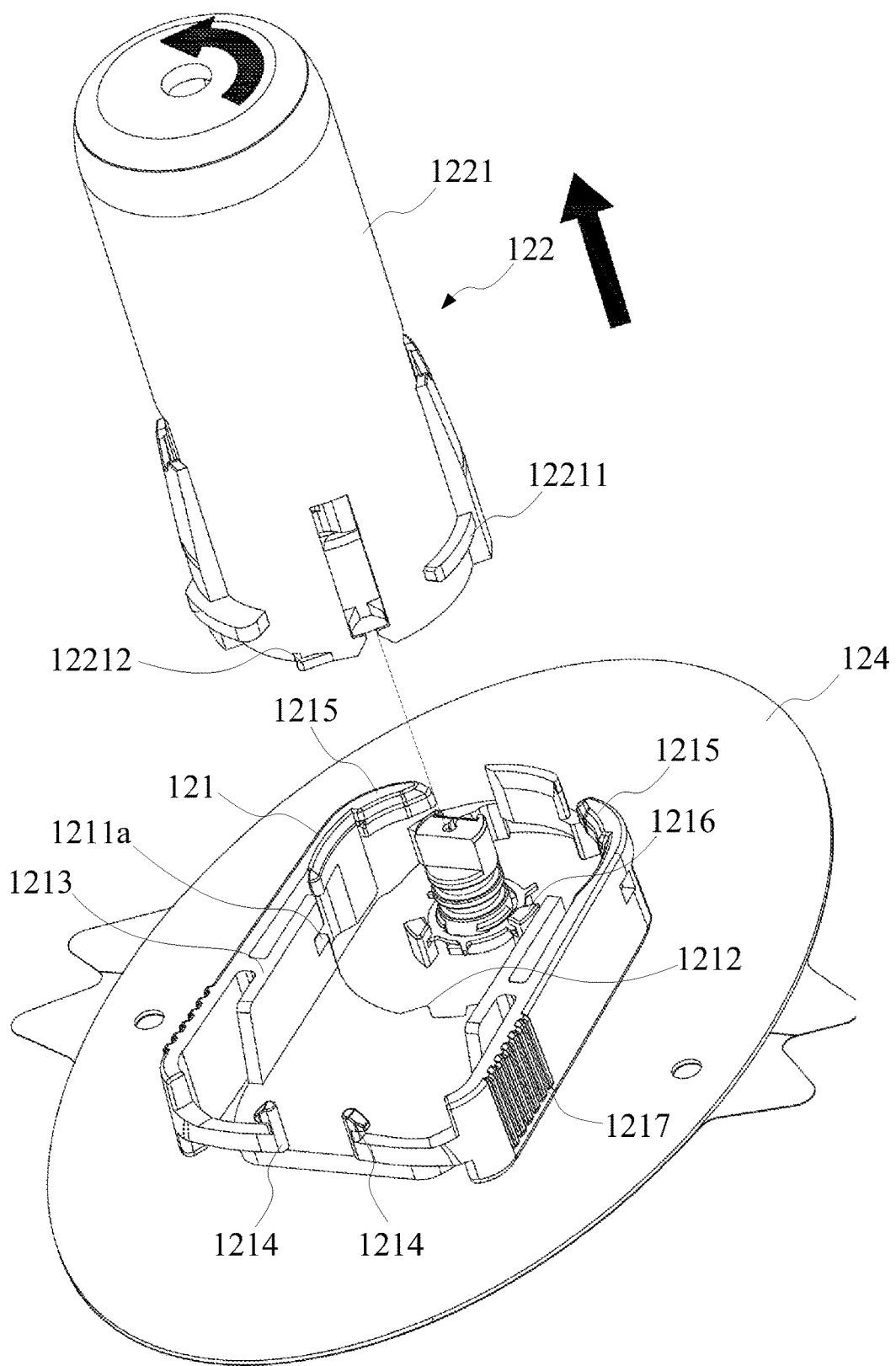
FIG. 6 illustrates an exploded view of a support mount and an inserter in an analyte sensing system according to present disclosure.

Referring to FIG. 4 to FIG. 6, FIG. 4 illustrates a schematic diagram of a support mount in an analyte sensing system according to present disclosure, FIG. 5 illustrates a schematic diagram of a shell in an analyte sensing system according to present disclosure, FIG. 6 illustrates an exploded view of a support mount and an inserter in an analyte sensing system according to present disclosure. As shown in FIG. 4, the support mount and the medical adhesive tape are connected. As shown in FIG. 6, the support mount 121 includes a first installation structure configured to accommodate the inserter 122, a second installation structure configured to accommodate the transmitter 13, and a third installation structure configured to accommodate a sensor probe shell 125.

The inserter 122 is located on the first installation structure, and the inserter 122 includes an inserter shell 1221 (illustrated in FIG. 5), an ejection mechanism 122, and a button module 1223.

The first installation structure includes a first sliding unit 1211a, a second sliding unit 1211b, and a first fastener unit 1212. Correspondingly, a third sliding unit 12211a, a fourth sliding unit 12211b corresponding to the first sliding unit 1211a, the second sliding unit 1211b, and a second fastener unit 12212 corresponding to the first fastener unit 1212, which are arranged on a bottom edge of the inserter shell 1221. Specifically, the first sliding unit 1211a and the second sliding unit 1211b are a slideway and a sliding groove, and the third sliding unit 12211a and the fourth sliding unit 12211b are a sliding beam and a sliding clock corresponding to the slideway and the sliding groove, where the sliding beam and sliding clock are integrated on the outer surface of the inserter shell 1221; the first fastener unit 1212 is a fastener, and the second fastener unit 12212 is also a fastener and can form a fastened structure with the first fastener unit 1212.

A flange 1213 and an operating unit are arranged on each of opposite inner sides of the second installation structure, a cantilever 1215 and a clamping hook 1214 are respectively arranged in front and rear ends of each of the operating units, and a pressing unit (corresponding to reference sign 1217 in FIG. 6) is arranged in rear ends of the operating units, where when the pressing unit 1217 is pressed, the pressing unit drives the two sided cantilevers 1215 to an open state; the cantilevers 1215 are configured to jam the inserter shell 1221 when the inserter 122 is installed, while the cantilevers 1215 are also configured to jam the shell of the transmitter 13 when the transmitter 13 is installed, which will be detailed in the following contents.

Figure 7:
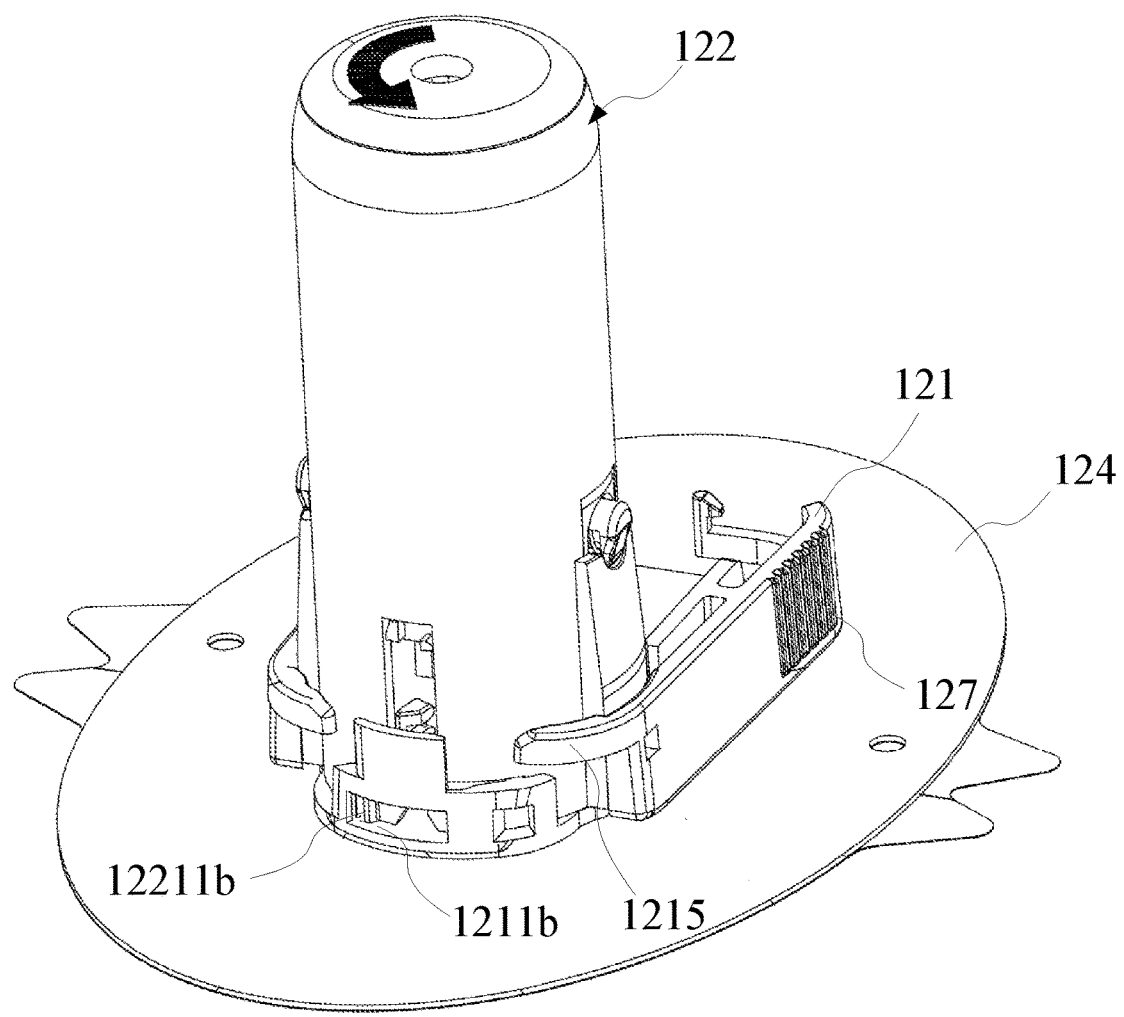
FIG. 7 illustrates a combined an inserter and a support mount in an analyte sensing system according to present disclosure.

In the actual operation process, referring to FIG. 7, a combined an inserter and a support mount in an analyte sensing system according to present disclosure is illustrated. As shown in FIG. 7, two cantilevers 1215 of the support mount 121 jam the inserter shell 1221 and prevent the inserter shell 1221 from rotating left or right; the third sliding unit 12211a and the fourth sliding unit 12211b of the inserter shell 1221 is arranged in the first sliding unit 1211a and the second sliding unit 1211b of the support mount 121, which will prevent the inserter shell 1221 and the support mount 121 from loosening up or down and separating. When the analyte sensing system is used (when the inserter 122 is needed to remove from the support mount 121), one hand of the user presses the pressing unit 1217 on the support mount 121 to open the cantilevers 1215, and then rotation restriction of the inserter shell 1221 is relieved. The other hand of the user rotates anticlockwise the inserter shell 1221 in the direction of an arrow on the inserter shell 1221, until the user hears a "snap" product by separating the first fastener unit 1212 from the second fastener unit 12212, and the inserter shell 1221 cannot be rotated. When the inserter shell 1221 is rotated to the specified position, the first fastener unit 1212 and the second fastener unit 12212 separate from each other, and the inserter 122 and the support mount 121 are separated, and then the inserter 122 can be vertically removed from the support mount 121.

Figure 8:
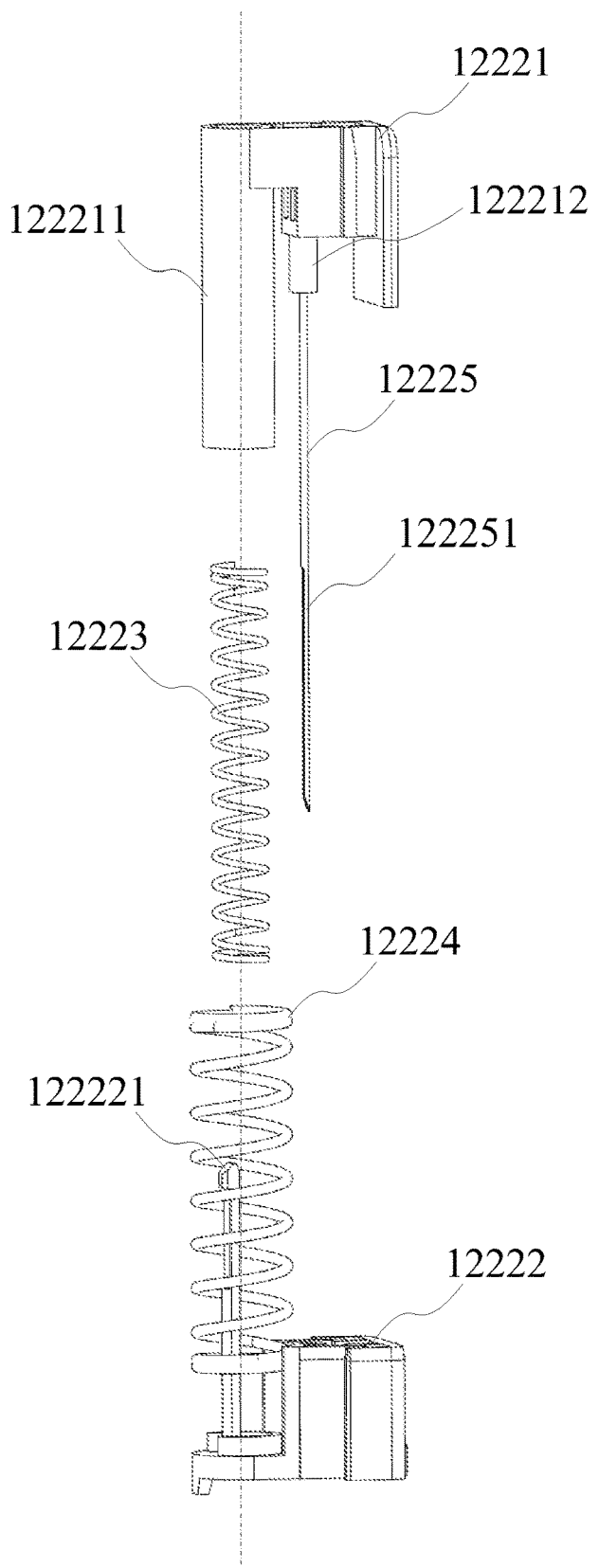
FIG. 8 illustrates an exploded view of an ejection mechanism in an analyte sensing system according to present disclosure.
Figure 9:
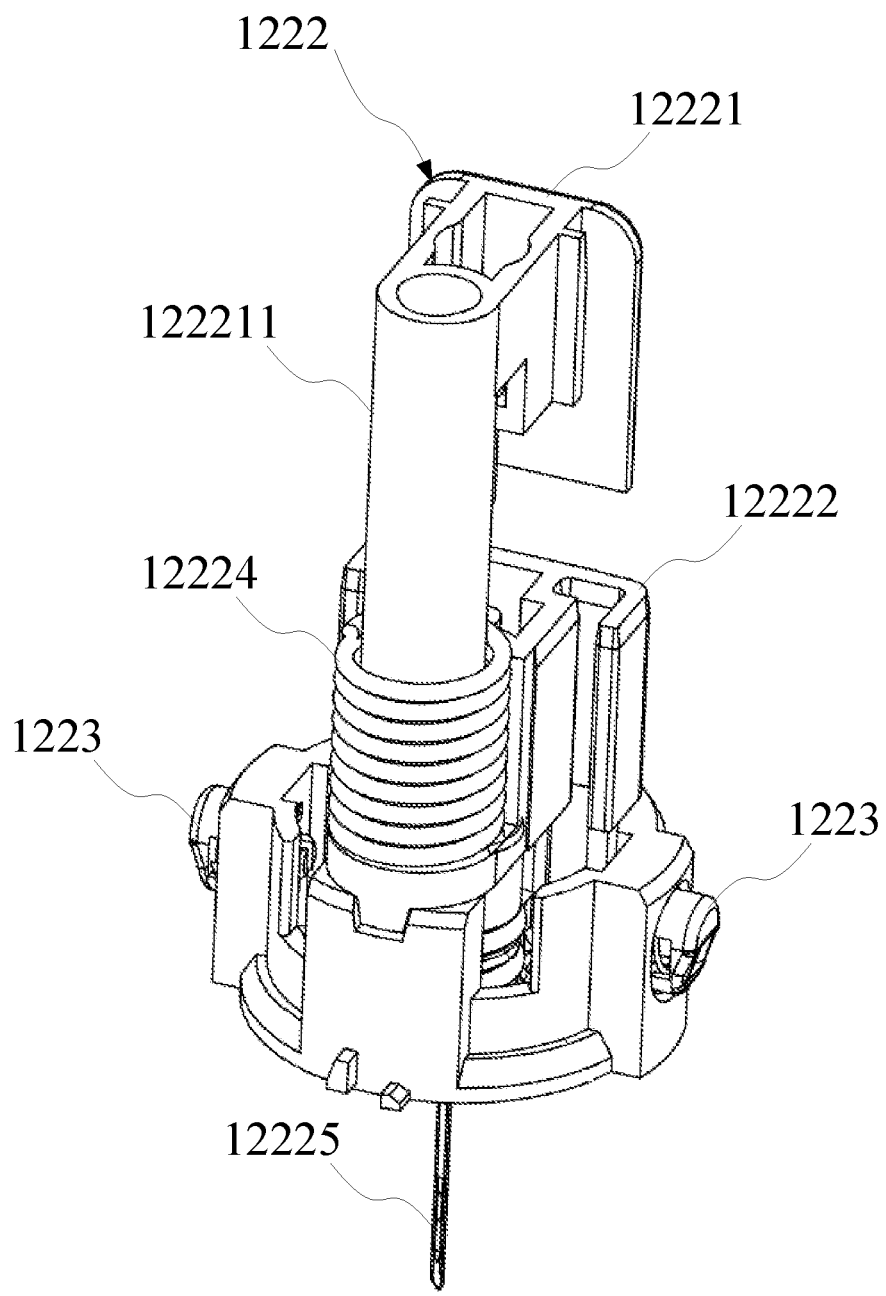
FIG. 9 illustrates a combined an ejection mechanism, a button module and a sensor probe shell in an analyte sensing system according to present disclosure.
Figure 10:
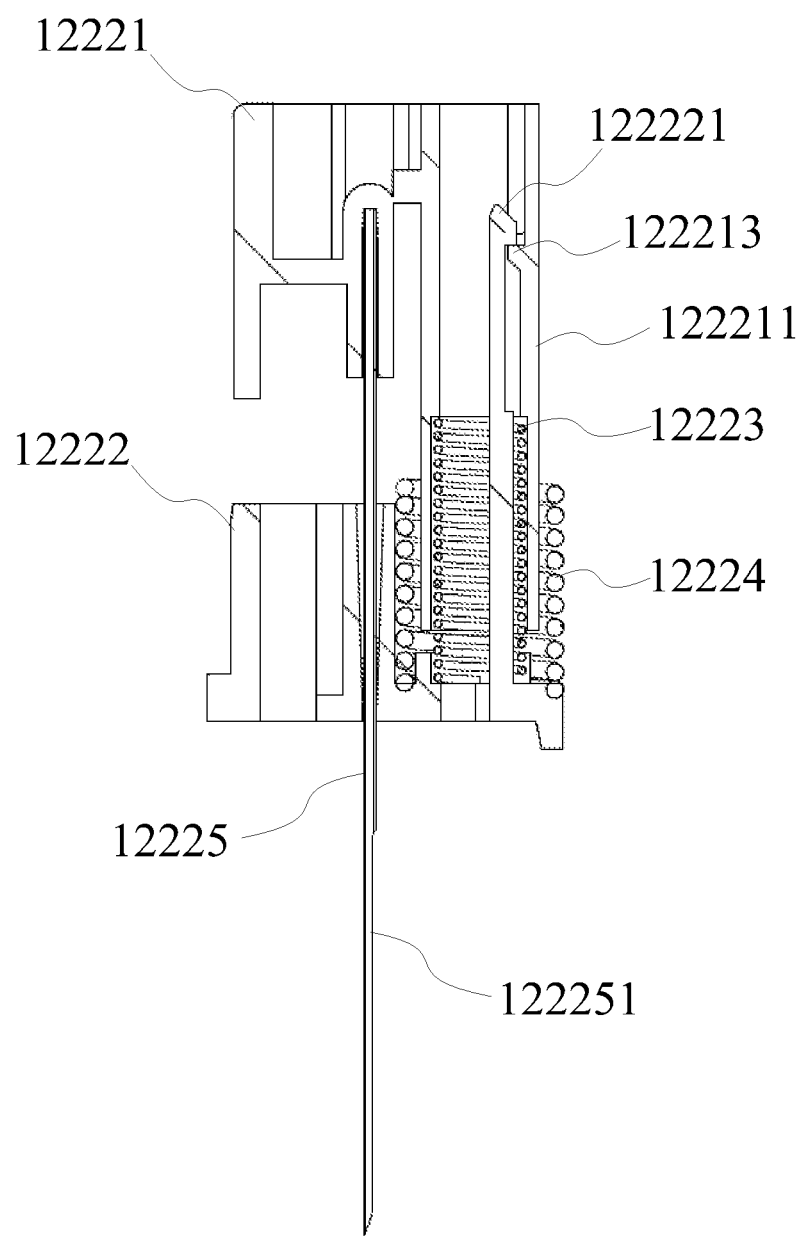
FIG. 10 illustrates a cross-sectional view of an ejection mechanism in an analyte sensing system according to present disclosure.

Referring to FIG. 8 to FIG. 10, FIG. 8 illustrates an exploded view of an ejection mechanism in an analyte sensing system according to present disclosure, FIG. 9 illustrates a combined an ejection mechanism, a button module and a sensor probe shell in an analyte sensing system according to present disclosure, and FIG. 10 illustrates a cross-sectional view of an ejection mechanism in an analyte sensing system according to present disclosure. An ejection mechanism 1222 is arranged inside the inserter shell 1221, where the ejection mechanism includes: a first sliding block 12221, a second sliding block 12222, an inner spring 12223, an outer spring 12224 and a puncture needle 12225.

The first sliding block 12221 includes a hollow guide column 122211 arranged vertically, a needle bed 122212 paralleled to the hollow guide column 122211, and a first locking part 122213 located on an inner wall of the hollow guide column 122211, where an ejection space is set in an interior of the hollow guide column, and the first locking part 122213 is a bump.

The second sliding block 12222 is set corresponding to the first sliding block, and includes a second locking part 122221 locked with the first locking part 12221, where the second locking part 122221 penetrates through the internal of the hollow guide column 12211. The second locking part 122221 is clamping hook corresponding to the bump, and the first locking part 12221 and the second locking part 122221 are fastened, when they are connected.

The inner spring 12223 is located in the ejection space, where two ends of the inner spring 12223 are clung between the first sliding block 12221 and the second sliding block 12222, when the inner spring 12223 releases, the inner spring 12223 drives the first sliding block 12221 to rise.

Figure 11:
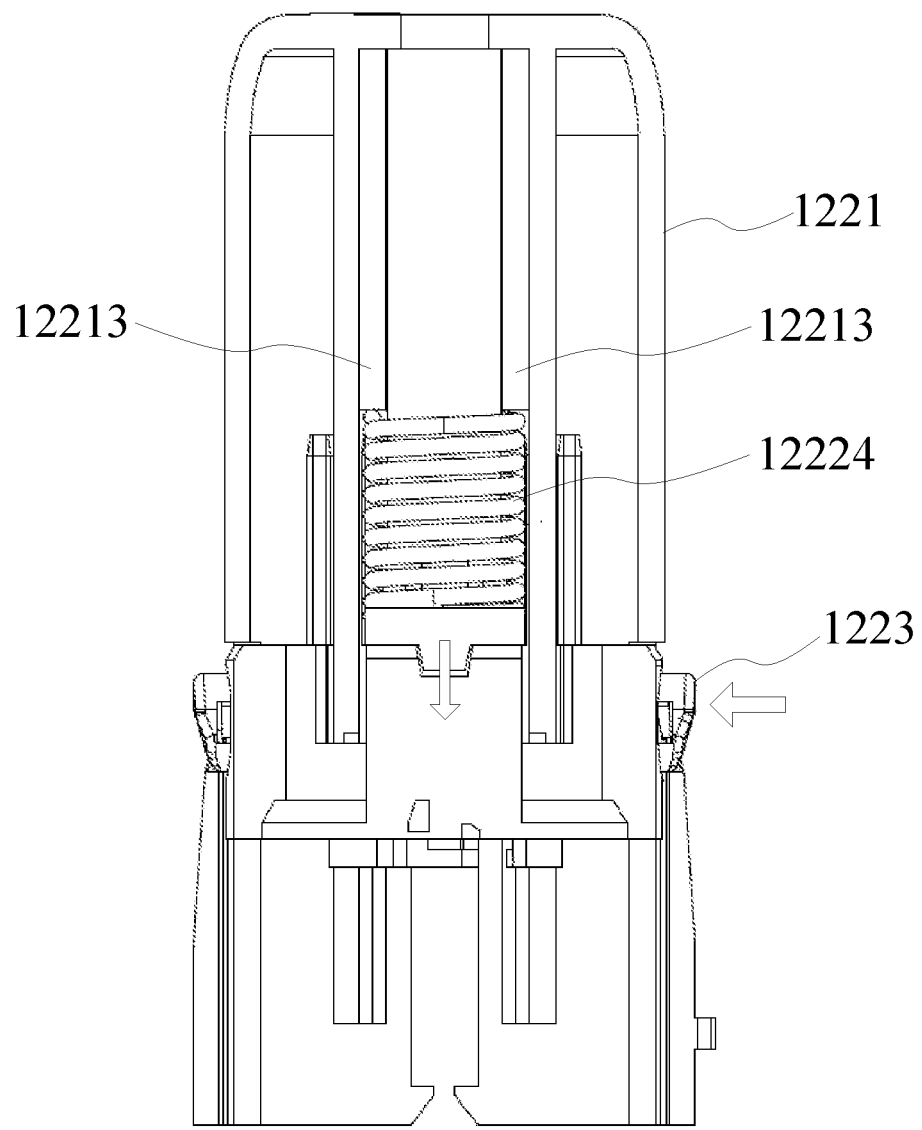
FIG. 11 illustrates a combined an outer spring and a shell in an analyte sensing system according to present disclosure.

The outer spring 12224 is arranged circumferentially outside of the hollow guide column, where two ends of the outer spring 12224 are clung between the second sliding block 12222 and baffles 12213 located in the inserter shell 1221, when the outer spring 12224 releases, the outer spring 12224 drives the first sliding block 12221, the inner spring 12223 and the second sliding block 12222 to descend. As shown in FIG. 11, a combined an outer spring and a shell in an analyte sensing system according to present disclosure is illustrated.

The top of the puncture needle 12225 is fixed inside the needle bed 122212, where the body of the puncture needle 12225 has a puncture part 122251, the body of the puncture needle 12225 penetrates through the second sliding block 12222 and extends outside of the second sliding block 12222, when the outer spring 12224 releases, the puncture needle 12225 impales downward, and when the inner spring 12223 releases, the puncture needle 12225 is pulled out upward. The sensor probe is arranged in the puncture part 122251. Specifically, the puncture part 122251 is arranged on an end of the puncture needle 12225, and the cross section of the puncture part 122251 is curved, a sensing part of the sensor probe is configured to detect the glucose content in the human body, where the sensing part is arranged in the puncture part 122251, when the outer spring 12224 releases, the puncture needle 12225 impales the skin of the human body downward, and then the sensing part is implanted subcutaneously with the puncture needle 12225 together, when the inner spring 12223 releases, the puncture needle 12225 is pulled out upward, and then the sensing part is indwelt in the skin of human body and realizes the detection and collecting of the glucose content.

The button module 1223 is configured to release the ejection mechanism, where the button module includes two buttons located on the opposite sides of the inserter shell 1221, when the buttons are triggered, the outer spring 12224 releases. When the outer spring 12224 releases, the first locking part 122213 and the second locking part 122221 is released to be unlocked, and then the inner spring also releases.

Figure 12:
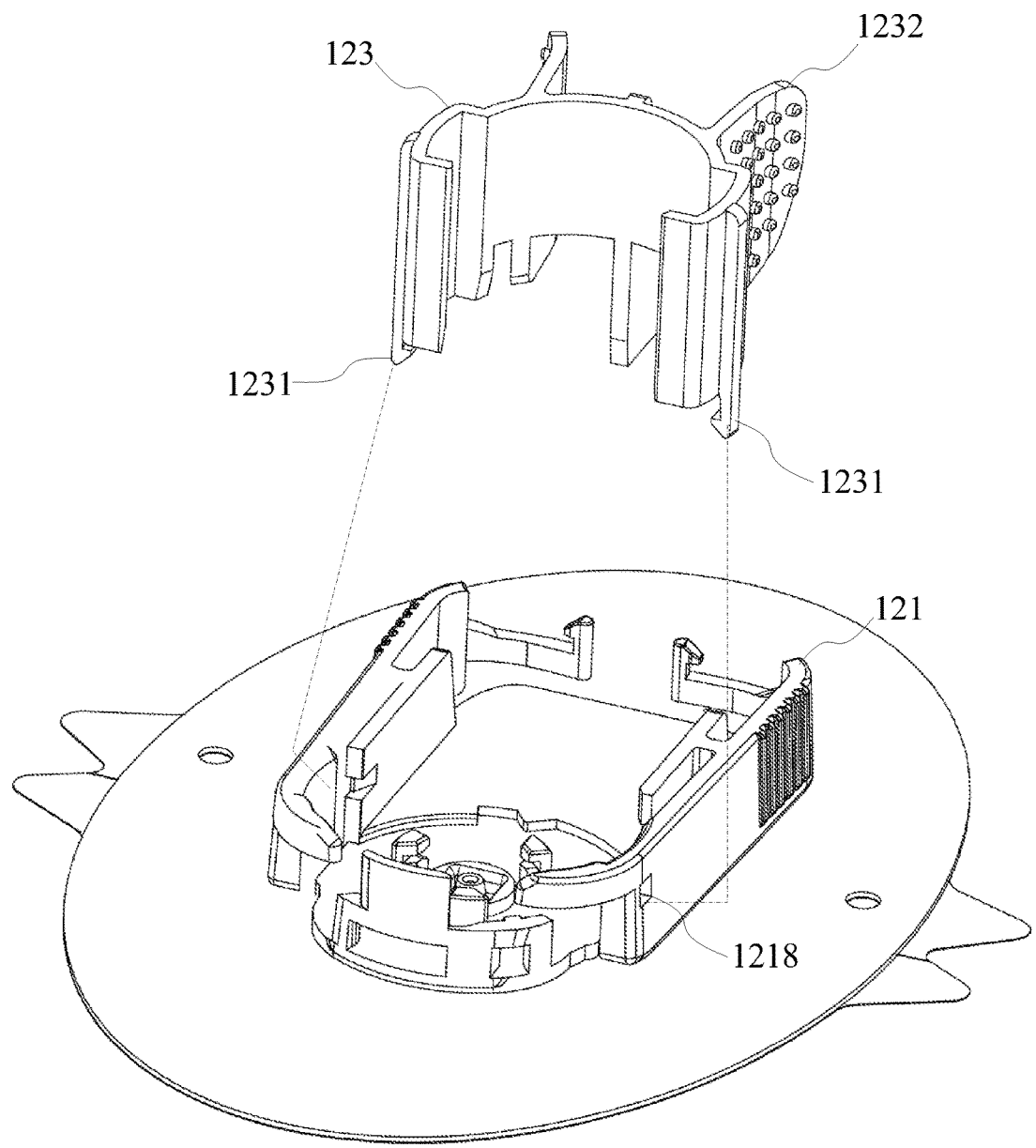
FIG. 12 illustrates an exploded view of a support mount and a safety lock in an analyte sensing system according to present disclosure.
Figure 13:
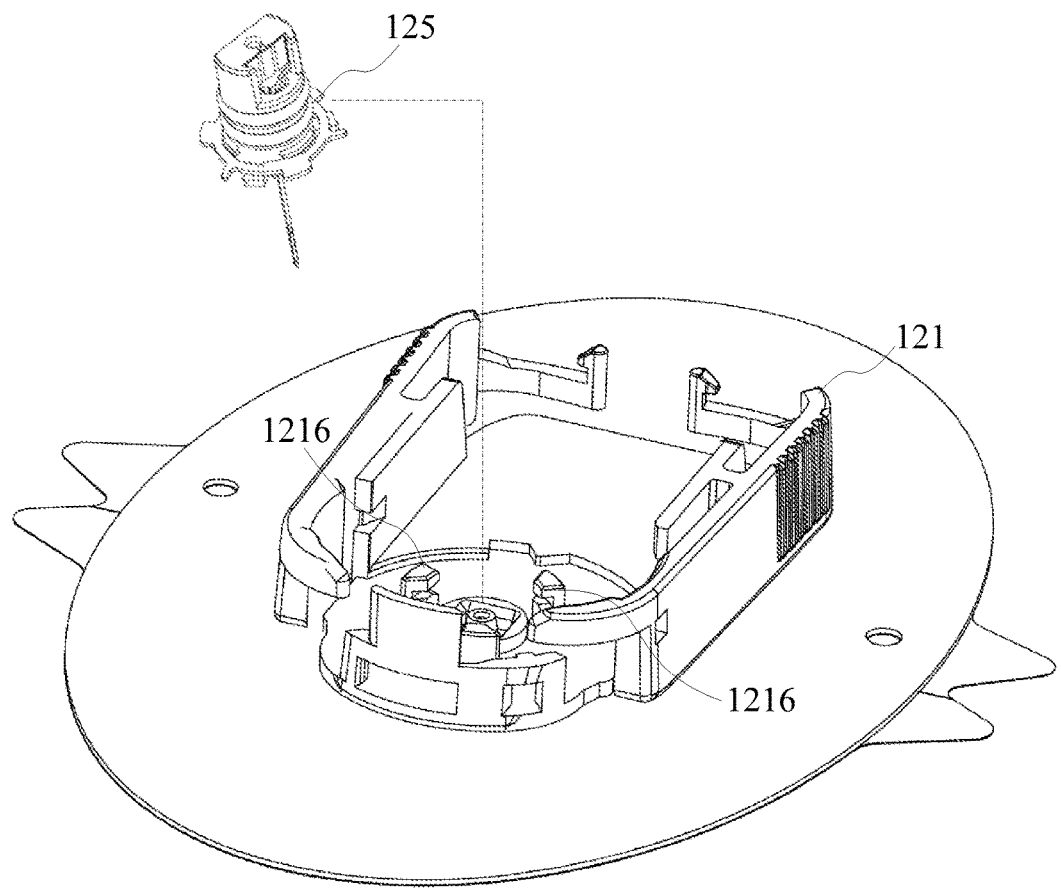
FIG. 13 illustrates an exploded view of a sensor probe shell and a support mount in an analyte sensing system according to present disclosure.

In some embodiments, referring to FIG. 12, an exploded view of a support mount and a safety lock in an analyte sensing system according to present disclosure is illustrated. As shown in FIG. 12, a slot 1218 is arranged on the support mount 121, a clamping hook 1231 corresponding to the slot 1218 is arranged on the safety lock 123. An operating handle 1232 configured to control the clamping hook 1231 to separate from the slot 1218 is arranged on the safety lock 123. The safety lock is arranged on the shell, and is configured to cover the button module 1223 and prevent the button module from mistakenly pressing, and the mistakenly pressing will trigger the ejection mechanism 1222 in the inserter 122. A schematic diagram of the safety lock 123 that covers the button module 1223 is illustrated in FIG. 3.

Referring to FIG. 11, at the initial time, the outer spring 12224 is in the compression state, and the inner spring 12223 is also in the compression state. After they were triggered by the external force, the outer spring 12224 in the outer ring releases and divers the ejection mechanism to go forward, and then the puncture needle 12225 impales the skin of human body. When the ejection mechanism moves to the specified position, the locking state of the first locking part 122213 and the second locking part 122221 is released, and then the inner spring 12223 in the inner ring also releases, the first sliding block 12221 and the puncture needle 12225 are pushed back along the original path, that is the puncture needle 12225 is pulled out from the human body. So, the ejection mechanism instantaneously completes puncturing and pulling out.

As shown in FIG. 7 to FIG. 9, the button module 1223 and the second sliding block 12222 cooperate with each other, the buttons are wadge, and the buttons are out of the inserter shell 1221. At the initial time, the thin place of the button is stuck state with the inserter shell 1221; after the buttons are pressed, the buttons move inward and release the stuck state. At the same time, because the outer spring 12224 is in the compression state (the outer spring 12224 is resist against the second sliding block 12222 and baffles 12213 located in the inserter shell 1221), the outer spring 12224 releases and divers the second sliding block 12222 to descend, and the drives the ejection mechanism to descend.

Figure 14:
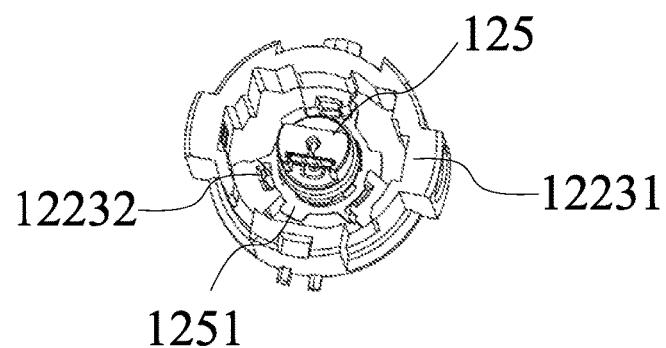
FIG. 14 illustrates a combined a sensor probe shell and a button support mount in an analyte sensing system according to present disclosure.
Figure 15:
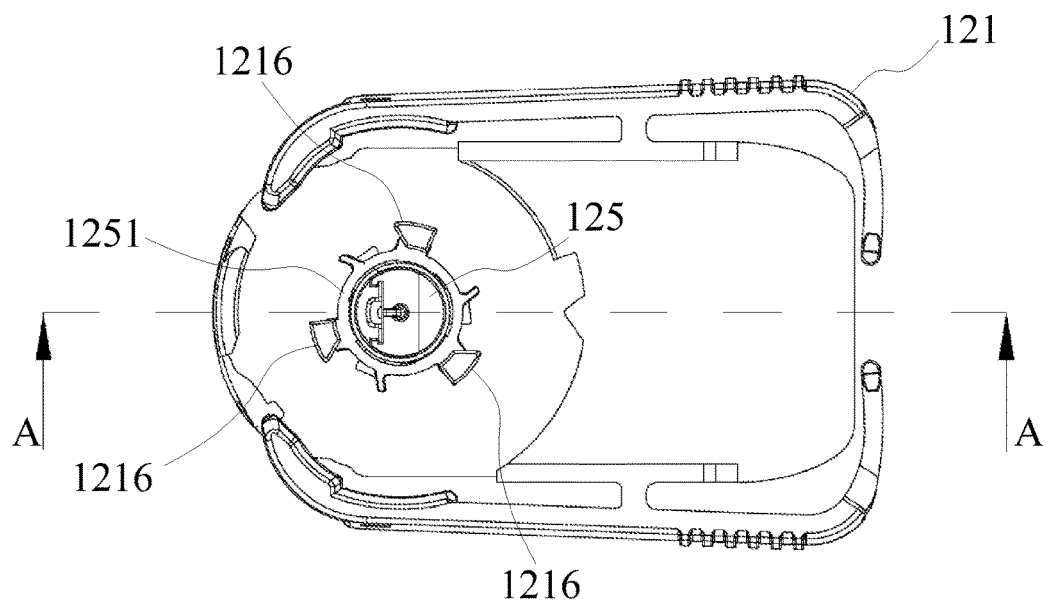
FIG. 15 illustrates a top view of a sensor probe shell and a support mount in an analyte sensing system according to present disclosure.
Figure 16:
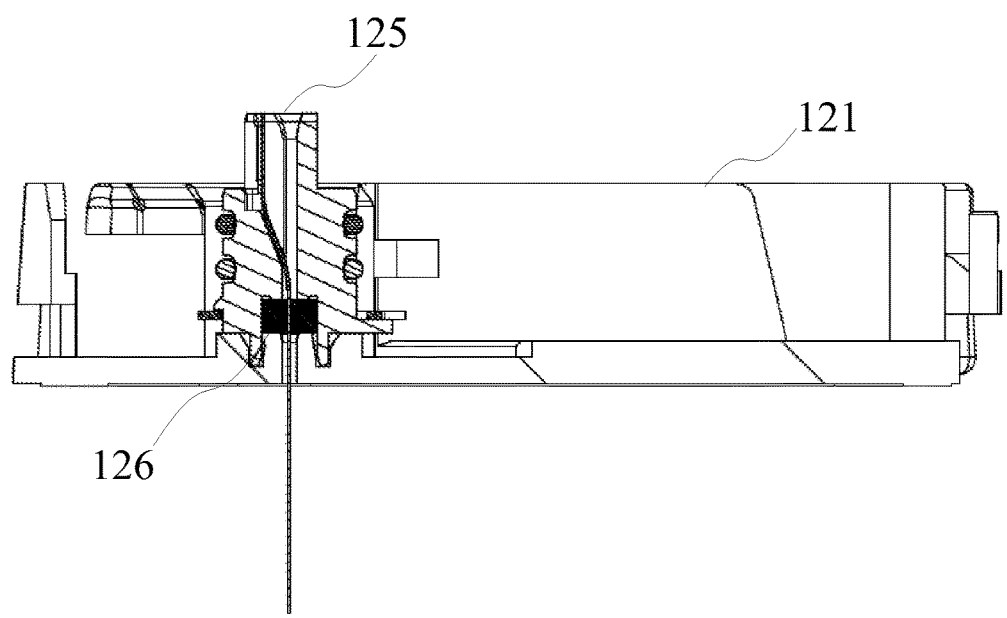
FIG. 16 illustrates a view in section on A-A of FIG. 15.

Referring to FIG. 13 to FIG. 16, FIG. 13 illustrates an exploded view of a sensor probe shell and a support mount in an analyte sensing system according to present disclosure; FIG. 14 illustrates a combined a sensor probe shell and a button support mount in an analyte sensing system according to present disclosure; FIG. 15 illustrates a top view of a sensor probe shell and a support mount in an analyte sensing system according to present disclosure; FIG. 16 illustrates a view in section on A-A of FIG. 15. As shown in FIG. 14, the third installation structure includes three fixture blocks 1216, and the sensor probe shell 125 is arranged in a structure formed by the three fixture blocks. Before the sensor probe shell 125 is installed, the sensor probe shell 125 is fixed in the button support mount 12231 by three slots located on the button support mount 12231 and the three fasteners located on the sensor probe shell 125 (as shown in FIG. 14, the slots 12232 are a part of the button support mount 12231, and the fixture blocks 1216 are a part of the support mount), and the sensor probe shell 125 is limited by a clasp 1251. As shown in FIG. 15, after the sensor probe shell 125 is installed, the sensor probe shell 125 is fixed on the support mount 121 by fastening the clasp 1251 and the fixture blocks 1216 located on the support mount 121. As shown in FIG. 16, a silica gel plug 126 is arranged between the sensor probe shell 125 and the support mount 121, and the silica gel plug 126 is squeezed by the sensor probe shell 125 and the support mount 121 to prevent the water passing through and achieve waterproof function.

Figure 17:
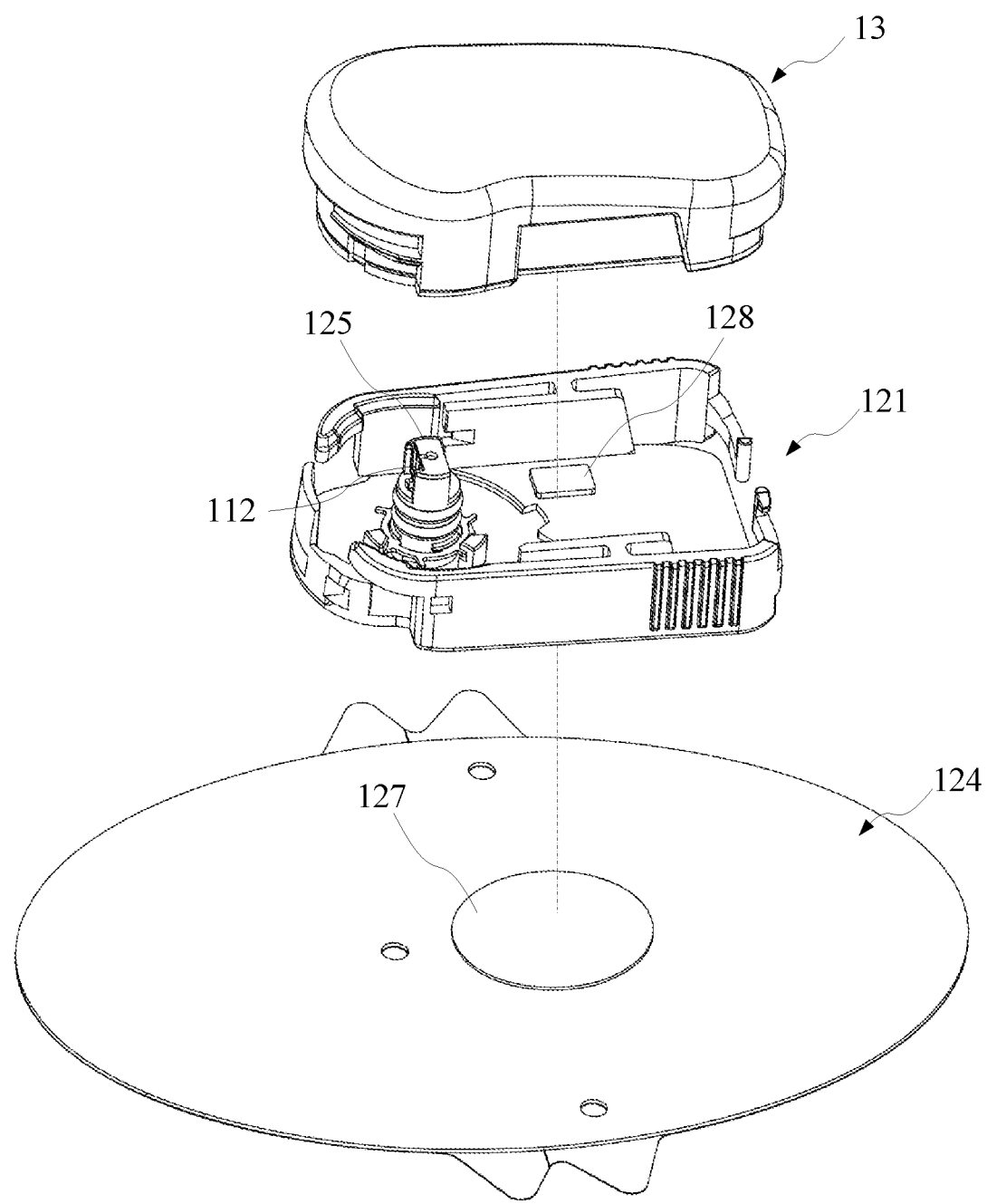
FIG. 17 illustrates an exploded view of a transmitter, a support mount and a medical adhesive tape in an analyte sensing system according to present disclosure.

After the sensor probe shell 125 is arranged on the support mount 121 (need to be explained, when the inserter 122 is removed, the ejection mechanism and the button module 1223 are removed together, but the sensor probe shell 125 is left on the support mount 121) and a transmitter is installed, the analyte sensing system may work. Referring to FIG. 17, an exploded view of a transmitter, a support mount and a medical adhesive tape in an analyte sensing system according to present disclosure is illustrated. The transmitter is connected to the sensor probe. Specifically, an electric conductor (not shown) is arranged on the sensor probe shell 125, the electric conductor contacts a connecting device (not shown) in the transmitter 13 to product a short signal configured to identify a connection state of the sensor probe 11 and the transmitter 13, after the sensor probe 11 and the transmitter 13 are coupled.

The transmitter 13 and the sensor probe 11 achieve communication connection by the connecting part 112 (PAD) of the sensor probe 11. Where the transmitter 13 is configured to receive the glucose content information transmitted by the sensor probe 11 implanted subcutaneously, convert the glucose content information into a radio signal and output the radio signal, while the transmitter 13 is configured to receive the glucose content information transmitted by the sensor probe 11 implanted subcutaneously, convert the glucose content information into a radio-frequency signal (RF signal) and output the radio-frequency signal (RF signal). A processor and a control circuit (not shown) are embedded in the transmitter 13.

In some embodiments, the analyte sensing system further includes an automatic relay system configured to convert the radio-frequency signal into a 2G/3G signal, a Bluetooth signal, or a wireless fidelity (WIFI) signal. In general, the transmitter transmits the signal directly to the receiver, and the receiver can receive and identify the signal. However, when the receiver cannot receive and identify the signal, the automatic relay system will be required to convert the signal into a signal that can be identified by the receiver. The automatic relay system and the transmitter realize communications via a radio signal.

In some embodiments, the automatic relay system further includes an alarm apparatus (not shown), and the automatic relay system may identify the abnormal event such as hypoglycemia, hyperglycemia, etc. and alarm the user. In addition, the automatic relay system further also includes a display screen (not shown) for displaying the abnormal event.

Figure 19:
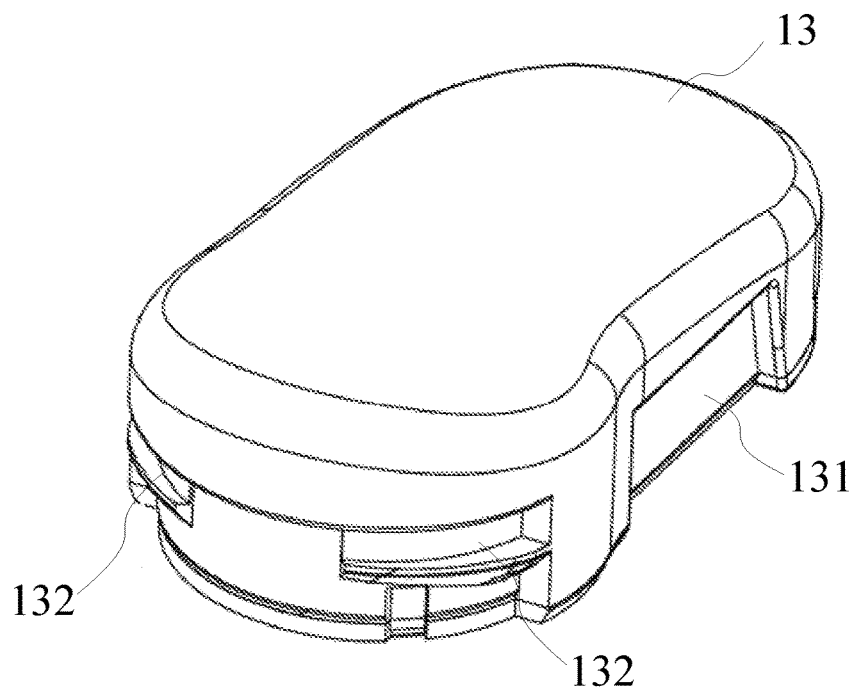
FIG. 19 and FIG. 20 illustrate two angles of view of a transmitter in an analyte sensing system according to present disclosure.

In the structure of FIG. 17, an identification module 128 configured to identify a connection state of the sensor probe 11 and the transmitter 13 is arranged on the support mount 121. In some embodiments, the identification module 128 is a magnetic switch. Specifically, the identification module 128 includes a magnet on the support mount 121, when the transmitter 13 is arranged on the support mount 121, the chip in the transmitter 13 and the magnet produce attraction, and then the connection state of the sensor probe 11 and the transmitter 13 are identified; or the connection state of the sensor probe 11 and the transmitter 13 are identified by the a short signal produced by coupling the sensor probe 11 and the transmitter 13 (as shown in FIG. 19). An electric conductor (not shown) is arranged on the sensor probe shell 125, the electric conductor contacts a connecting device in the transmitter 13 to product a short signal for identifying a connection state of the sensor probe 11 and the transmitter 13, when the sensor probe 11 and the transmitter 13 are coupled.

Figure 18:
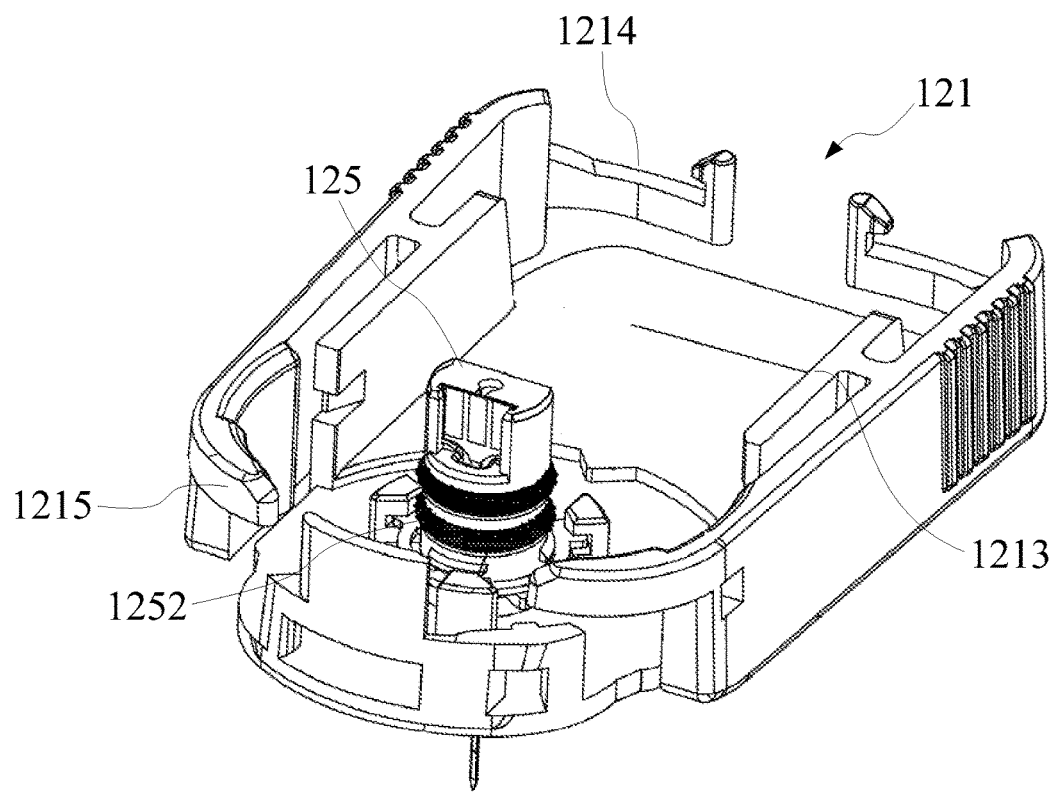
FIG. 18 illustrates a schematic diagram of a support mount with a sensor probe in an analyte sensing system according to present disclosure.
Figure 20:
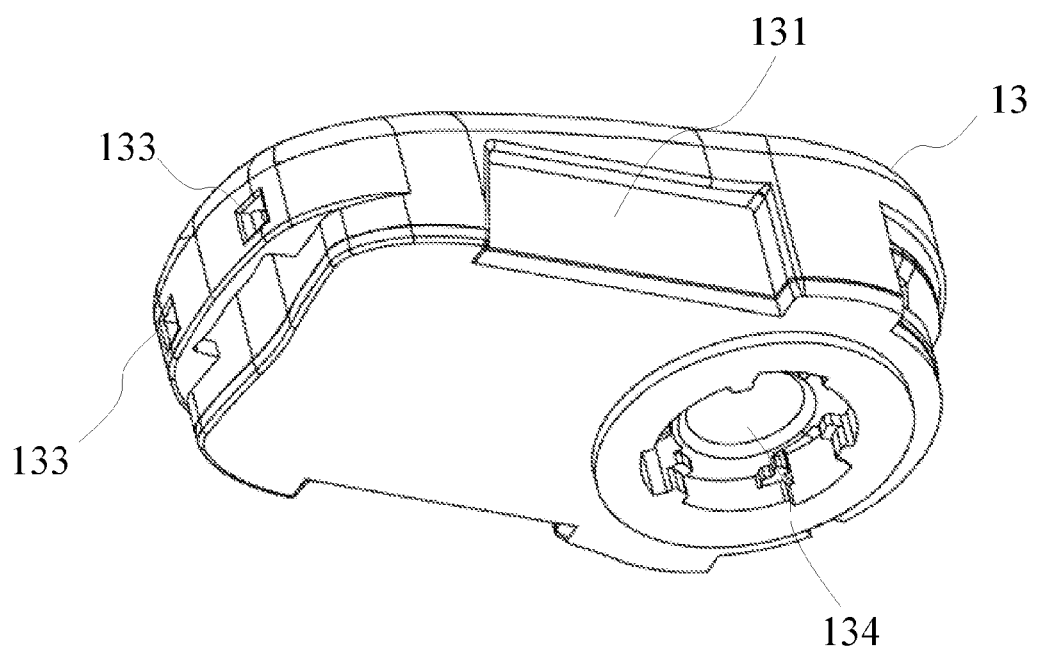
Figure 21:
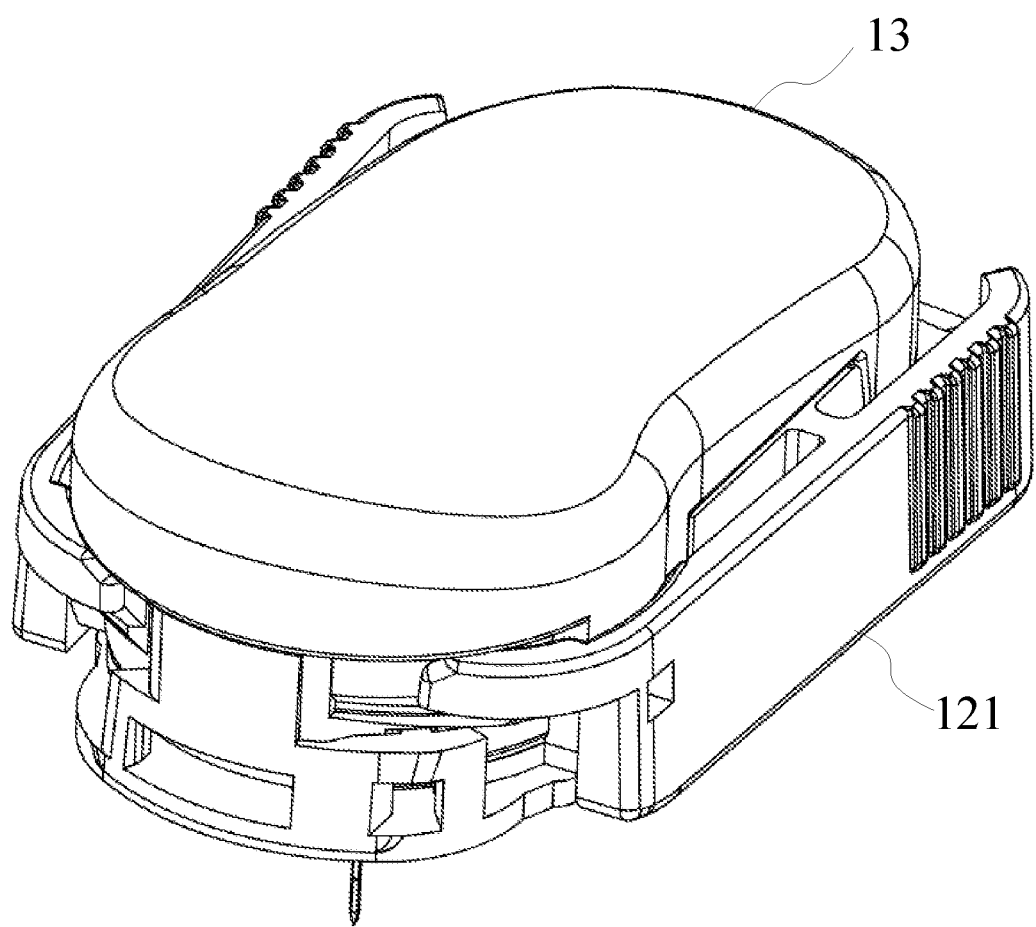
FIG. 21 illustrates a combined a transmitter and a support mount in an analyte sensing system according to present disclosure.

Referring to FIG. 18, a schematic diagram of a support mount with a sensor probe in an analyte sensing system according to present disclosure is illustrated. As shown in FIG. 18, two O-shaped sealing rings 1252 arranged on the sensor probe shell 125 and a seal cavity (134 of FIG. 20) located under the shell of the transmitter 13 are used together to achieve waterproof function. Referring to FIG. 19 and FIG. 20, two angles of view of a transmitter in an analyte sensing system according to present disclosure are illustrated. As shown in FIG. 19 and FIG. 20, grooves 131 corresponding to the flange 1213 are respectively arranged in two sides of an outer edge of the transmitter 13, and slots 132, 133 corresponding to the cantilever 1215 and clamping hook 1214 are respectively arranged in front and rear ends of the transmitter. As shown in FIG. 20, the transmitter has a seal cavity 134 configured to accommodate the sensor probe shell 125. When the transmitter 13 is installed, the grooves 131 is guided to slide into the flange 1213 located on the support mount 121, which can play a limiting role and prevent the transmitter 13 from sliding left or right. When the transmitter 13 is being slid into the flange 1213, the cantilever 1215 of the support mount and the clamping hook 1214 located the rear end of the transmitter are automatically opened, while when the transmitter 13 slides into the terminal end of the flange 1213, the cantilever 1215 and the clamping hook 1214 restore to their original position and are fixed by cooperating with the slots 132 located in the front end of the transmitter 13 and the slots 133 located in the rear end of the transmitter 13, which prevent the transmitter 13 from moving up or down. Referring to FIG. 20, a combined a transmitter and a support mount in an analyte sensing system according to present disclosure is illustrated.

The probe installation device 12 further includes an identity recognition module 127 configured to recognize identity and store personalized information of the probe installation device, the sensor probe 11, or a combination thereof. As shown in FIG. 17, in some embodiments, the identity recognition module 127 is a near field communication (NFC) tag, a radio frequency identification (RFID) tag or an identity recognition chip. The identity recognition module 127 is located between the medical adhesive tape 124 and the support mount 121. In some embodiments, the identity recognition module is built in the support mount (not shown).

The receiver (not shown) is configured to receive the radio signal including the glucose content information transmitted by the transmitter, convert the glucose content information into glucose content data and display the glucose content data to a user. The receiver includes a display screen, a control circuit and a processor, and the transmitter may transmit the glucose monitoring information detected by the sensor probe to the receiver by wireless transmission receive mode. The control circuit and the processor are built in the receiver, and the receiver displays the glucose monitoring information to the user in the form of glucose values through a certain algorithm. In some specific embodiments, the receiver may be a smart mobilephone with a glucose monitoring program APP (application), or other intelligent terminal that can receive the information of the receiver (e.g., PDA). In some specific embodiments, the display screen may be a display screen support mountd on electronic paper breaking code display.

Although the present disclosure has been disclosed as above with reference to preferred embodiments thereof but will not be limited thereto. Those skilled in the art can modify and vary the embodiments without departing from the spirit and scope of the present disclosure. Accordingly, without departing from the scope of the present invented technology scheme, whatever simple modification and equivalent variation belong to the protection range of the present invented technology scheme.

What is claimed is:

1. An analyte sensing system, comprising:
   a sensor probe configured to detect an analyte content in a human body and transmit the detected analyte content information;
   a transmitter connected to the sensor probe, configured to receive the analyte content information transmitted by the sensor probe implanted subcutaneously, convert the analyte content information into a radio signal and output the radio signal;
   a receiver configured to receive the radio signal containing the analyte content information transmitted by the transmitter, convert the radio signal into analyte content data and display the analyte content data to a user; and
   a probe installation device configured to implant the sensor probe into a subcutis of the human body, wherein the probe installation device comprises a support mount, an inserter, a safety lock and a medical adhesive tape,
   wherein the support mount has an identification module arranged thereon, wherein the identification module is configured to identify a connection state of the sensor probe and the transmitter, and is a magnetic switch;
   wherein the support mount comprises a first installation structure configured to accommodate the inserter, a second installation structure configured to accommodate the transmitter, and a third installation structure configured to accommodate a sensor probe shell;
   wherein the probe installation device further comprises an identity recognition module configured to recognize identity and store personalized information of the probe installation device, the sensor probe, or a combination thereof, and the identity recognition module is a near field communication (NFC) tag, a radio frequency identification (RFID) tag or an identity recognition chip.

2. The analyte sensing system according to claim 1, wherein the inserter is located on the first installation structure, and the inserter comprises an inserter shell, an ejection mechanism arranged inside the inserter shell, and a button module configured to release the ejection mechanism;
   wherein the safety lock is located on the inserter shell and configured to cover the button module; and
   wherein the medical adhesive tape is connected to the support mount and configured to stick the support mount to a skin of the human body.

3. The analyte sensing system according to claim 2, wherein the first installation structure comprises a first sliding unit, a second sliding unit, and a first fastener unit; wherein the inserter shell comprises a third sliding unit, a fourth sliding unit and a second fastener unit which are arranged on a bottom edge of the inserter shell; wherein the third sliding unit and the fourth sliding unit are corresponding to the first sliding unit and the second sliding unit, respectively, and the second fastener unit is corresponding to the first fastener unit.

4. The analyte sensing system according to claim 2, wherein a flange and an operating unit are arranged on each of two opposite inner sides of the second installation structure, a cantilever and a clamping hook are respectively arranged at front and rear ends of each of the operating units, when the rear ends of the operating units are pressed, the two cantilevers are driven to an open state; wherein grooves corresponding to the flanges are respectively arranged on two sides of an outer edge of the transmitter, and slots corresponding to the cantilevers and the clamping hooks are respectively arranged at front and rear ends of the transmitter.

5. The analyte sensing system according to claim 2, wherein the third installation structure comprises multiple fixture blocks, and the sensor probe shell is arranged in a structure formed by the multiple fixture blocks.

6. The analyte sensing system according to claim 5, wherein a silica gel plug is arranged between the support mount and the sensor probe shell, and the silica gel plug is squeezed by the support mount and the sensor probe shell to form a sealed and waterproof structure.

7. The analyte sensing system according to claim 5, wherein the transmitter has a seal cavity configured to accommodate the sensor probe shell.

8. The analyte sensing system according to claim 5, wherein an electric conductor is arranged on the sensor probe shell, and the electric conductor is configured to: after the sensor probe and the transmitter are coupled, contact a connecting device in the transmitter to produce a short signal for identifying a connection state of the sensor probe and the transmitter.

9. The analyte sensing system according to claim 2, wherein a slot is arranged on the support mount, a clamping hook corresponding to the slot is arranged on the safety lock, and an operating handle configured to control the clamping hook to separate from the slot is arranged on the safety lock.

10. The analyte sensing system according to claim 2, wherein the ejection mechanism comprises:
   a first sliding block, comprising a hollow guide column which is vertically arranged, a needle bed parallel to the hollow guide column, and a first locking part located on an inner wall of the hollow guide column, wherein an ejection space is set in an interior of the hollow guide column;
   a second sliding block corresponding to the first sliding block, comprising a second locking part locked with the first locking part, wherein the second locking part penetrates through the interior of the hollow guide column;
   an inner spring located in the ejection space, wherein two ends of the inner spring resist against the first sliding block and the second sliding block, respectively, when the inner spring releases, the inner spring drives the first sliding block to rise;
   an outer spring arranged circumferentially outside of the hollow guide column, wherein two ends of the outer spring resist against the second sliding block and baffles located in the inserter shell, respectively, when the outer spring releases, the outer spring drives the ejection mechanism to descend; and
   a puncture needle, wherein a top end of the puncture needle is fixed inside of the needle bed, wherein the puncture needle has a puncture part, the puncture needle penetrates through the second sliding block and thus the puncture part extends outside of the second sliding block, when the outer spring releases, the puncture needle extends downwardly, and when the inner spring releases, the puncture needle is pulled upwardly.

11. The analyte sensing system according to claim 10, wherein the sensor probe comprises a sensing part configured to detect the analyte content in the human body and a connecting part connected to the transmitter, wherein the sensing part is arranged in the puncture part and is implanted subcutaneously with the aid of the puncture needle, wherein the puncture part is located at an end of the puncture needle, and the cross section of the puncture part is curved.

12. The analyte sensing system according to claim 10, wherein the button module comprises two buttons located on two opposite sides of the inserter shell, when the buttons are triggered, the outer spring and the inner spring are successively triggered to release, and the first locking part and the second locking part are released to be unlocked when either of the buttons is pressed.

13. The analyte sensing system according to claim 1, wherein the identity recognition module is located between the medical adhesive tape and the support mount, or embedded in the support mount.

14. The analyte sensing system according to claim 1, wherein a processor and a control circuit are embedded in the transmitter, and the receiver comprises a display screen, a control circuit and a processor.

15. The analyte sensing system according to claim 1, wherein the transmitter is configured to receive the analyte content information transmitted by the sensor probe, convert the analyte content information into a radio-frequency signal and output the radio-frequency signal.

16. The analyte sensing system according to claim 15, further comprising an automatic relay system configured to convert the radio-frequency signal into a 2G/3G signal, a Bluetooth signal or a wireless fidelity (WIFI) signal.

17. The analyte sensing system according to claim 16, wherein the automatic relay system further comprises an alarm apparatus.

18. The analyte sensing system according to claim 16, wherein the automatic relay system further comprises a display screen.

19. The analyte sensing system according to claim 1, wherein the identification module comprises a magnet on the support mount, and when the transmitter is arranged on the support mount, a chip in the transmitter and the magnet produce attraction to identify the connection state of the sensor probe and the transmitter; or
   where an electric conductor is arranged on the sensor probe shell, and when the sensor probe and the transmitter are coupled, the electric conductor contacts with a connecting component in the transmitter to produce a short signal to identify the connection state of the sensor probe and the transmitter.

* * * * *